United States Patent [19]
Lin

[11] Patent Number: 5,772,162
[45] Date of Patent: Jun. 30, 1998

[54] DROP-BOTTLE STAND

[76] Inventor: Chin-Liang Lin, No. 55, Chia-Tung Chiao, Chia-Fang Li, Hsin-Ying Hsih, Tainan Hsien, Taiwan

[21] Appl. No.: 730,781

[22] Filed: Oct. 16, 1996

[51] Int. Cl.[6] ...................................................... F16L 3/00
[52] U.S. Cl. ................... 248/121; 248/125.1; 248/125.8; 248/411
[58] Field of Search ................................ 248/121, 124.2, 248/125.1, 125.3, 125.8, 129, 159, 161, 411

[56] References Cited

U.S. PATENT DOCUMENTS

| | | | |
|---|---|---|---|
| 2,902,592 | 9/1959 | Cole et al. | 248/411 |
| 2,957,187 | 10/1960 | Raia | 248/125.1 |
| 4,596,484 | 6/1986 | Nakatani | 248/411 |
| 4,725,027 | 2/1988 | Bekanich | 248/125.8 |
| 4,744,536 | 5/1988 | Bancalari | 248/125.8 |
| 4,832,294 | 5/1989 | Eidem | 248/125.8 |
| 5,094,418 | 3/1992 | McBarnes, Jr. et al. | 248/308 |
| 5,125,607 | 6/1992 | Pryor | 248/125.1 |
| 5,385,323 | 1/1995 | Garelick | 248/161 |

*Primary Examiner*—Leslie A. Braun
*Assistant Examiner*—Anita M. King
*Attorney, Agent, or Firm*—Morton J. Rosenberg; David I. Klein; Jun Y. Lee

[57] ABSTRACT

A drop-bottle stand includes a base, a lower connecter, an outer tube, an inner movable tube extending and movable in the outer tube, an adjusting sleeve, a lower connecter, a cylindrical member, an upper connecter, a top hanging bar, an eccentric arm, and a plate. The inner movable tube can be moved up and down relative to the outer tube so as to adjust the height of the hanging bar by means of the eccentric arm, which can be swung to release or compress the plate and then the inner movable tube so as to free or tighten unmovable the inner tube for adjusting its position. The outer tube and the inner tube all have two opposite grooves to engage with each other to prevent the inner movable tue from moving rotatably.

1 Claim, 7 Drawing Sheets

DROP-BOTTLE STAND

BACKGROUND OF THE INVENTION

This invention concerns a drop-bottle stand, particularly easy to assemble or disassemble a top hanging bar so as to reducing dimensions of the whole stand for packing and transporting, and convenient for adjusting the height of the stand for hanging a drop bottle.

A drop-bottle stand is indispensable for a small clinic or a large hospital, and especially mobile ones are widely used. Manufacturers have attempted to produce them with least dimensions for lowering cost for both package and transportation. So various drop-bottle stands are in use and on market.

Two known conventional drop-bottle stands shown in FIGS. 8–11 are mobile height-adjustable ones. The first one shown in FIG. 8 includes a base 10, a lower connecter 11, an outer tube 12, an adjustable sleeve 13 and an inner movable tube 14 combined together. The base 10 has two elongate plates 101 combined to cross each other with a screw 103 passing through a central hole 102 bored in each plate 101, and a wheel 104 fixed under each of two ends of each plate 101 to stand and move freely on the ground. The lower connecter 11 is shaped cylindrical, having a hole 111 in a lower side, and a center hole 112 for a lower end of an outer tube 12 to fit in, placed on the intermediate portion of the base 10, and assembled with the ouer tube 12 and the base 10 by means of the screw 103 engaging with a threaded hole 121 of the outer tube 12.

The first known conventional drop-bottle further includes a cylindrical sleeve 13 fixed around an upper end of the outer tube 12 and having a side threaded hole 132 for a bolt 131 to manually engage with through a side hole of the outer tube 12 and to stick to an outer surface of an inner movable tube 14 for stopping the inner tube 14 after the inner tube 14 is adjusted in its position relative to the outer tube. And a top hanging bar 141 with two hooks 142 formed in two ends for hanging a drop bottle is fixed with an upper end of the inner tube 14.

The second known conventional drop-bottle shown in FIG. 10 includes an outer tube 12 having a stage of male threads 122 formed at an upper end, a ring unit 15 consisting of two rings 151 and an intermediate ring 152 with a swelled outer surface and fitting around the male threads 122, and adjusting sleeve 16 having an inner protruding edge 161 and female threads 162 and engaging with the male threads 122 so that an inner tube 14 may be adjusted in its position relative to the outer tube 12 by releasing or tightening the adjusting sleeve 16 as shown in FIG. 11.

However, the two known conventional drop-bottle stands just described have benn found to have the following disadvantages after a period of use.

1. The manually adjusted screw for sticking to the inner tube for stopping the inner tube is inconvenient to handle, and it easily causes a top hanging bar to fall down if a hand is released from it, permitting a drop bottle hung on the top hanging bar to sway violently, to a resultant possible accident and trouble.

2. The manually adjusted screw easily wears off, and the outer surface of the inner tube may be harmed to give rise to bruises, dents and bairy bits.

3. The second known conventional drop bottle stand has a rather complicated structure causing higher cost for a manufacturer.

4. The adjusting sleeve needs two hands in adjusting, and besides, the length for screwing in adjusting is rather long to take more time and laber.

5. If the inner movable tube is not gripped stably, it may rotate in adjusting process, and the top hanging bar may possible strike someone nearby, and in addition, a drop bottle may swing to and fro.

6. It is rather hard to decide whether the adjusting sleeve is rotated enough or not in tightening process. In case the sleeve is not surely tightened enough and hands are released from the sleeve and the inner tube, chances are that the inner movable tube with the drop bottle may fall down suddenly.

7. the inner movable tube and the top hanging bar are welded together, impossible to fold them to necessitate a large package and thus heighten cost for packaging and transporting.

8. Medical instruments are mostly made of stainless steel, for fear of growing rusts, and stainless steel is hard to weld. Even welded, the welded portion should be cleaned and treated for preventing rusts, heightening cost. In case common steel is used as material, it should be treated with plating and rustpreventing process, also increasing cost.

SUMMARY OF THE INVENTION

The purpose of the invention is to offer a drop bottle stand having a simple structure in adjusting height of the stand for hanging a drop bottle.

One feature of the invention is an adjusting sleeve pivotally combined with an eccentric arm swingable so that the eccentric arm is swung to contact a plate, which in turn compresses and keeps unmovable an inner movable tube at one of many positions relative to an outer tube in adjusting height of the stand.

Another feature of the invention is two longitudinal grooves provided in the inner movable tube and the outer tube to engage with each other so that the inner movable tube may not rotate during adjusting the position of the inner movable tube relative to the outer tube, and thus a drop bottle may not sway to and fro in an adjusting process.

Another feature of the invention is an eccentric arm swingable from a loosening position to a tightening position or vice versa for the inner movable tube, and the distance between the two positions is very short and definite for any layman to handle easily, without any possibility that the inner movable tube together with the top hanging bar falls down in case of hands released.

Another feature of the invention is an upper connecter and a top hanging bar deposited on the upper connecter. The top hanging bar is easily assembled with or disassembled from the inner movable tube via the upper connecter for minimizing dimensions of the whole stand for packaging and transporting.

One more feature of the invention is an elastic button for assembling the upper connecter with the inner movable tube with ease and secured at its position stably, keeping the upper connecter with the top handing bar in a stable position.

BRIEF DESCRIPTION OF DRAWINGS

The invention will be better understood by reference to the accompanying drawings, wherein.

DESCRIPTION OF THE PREFERRED EMBODIMENTS

Figure 1:
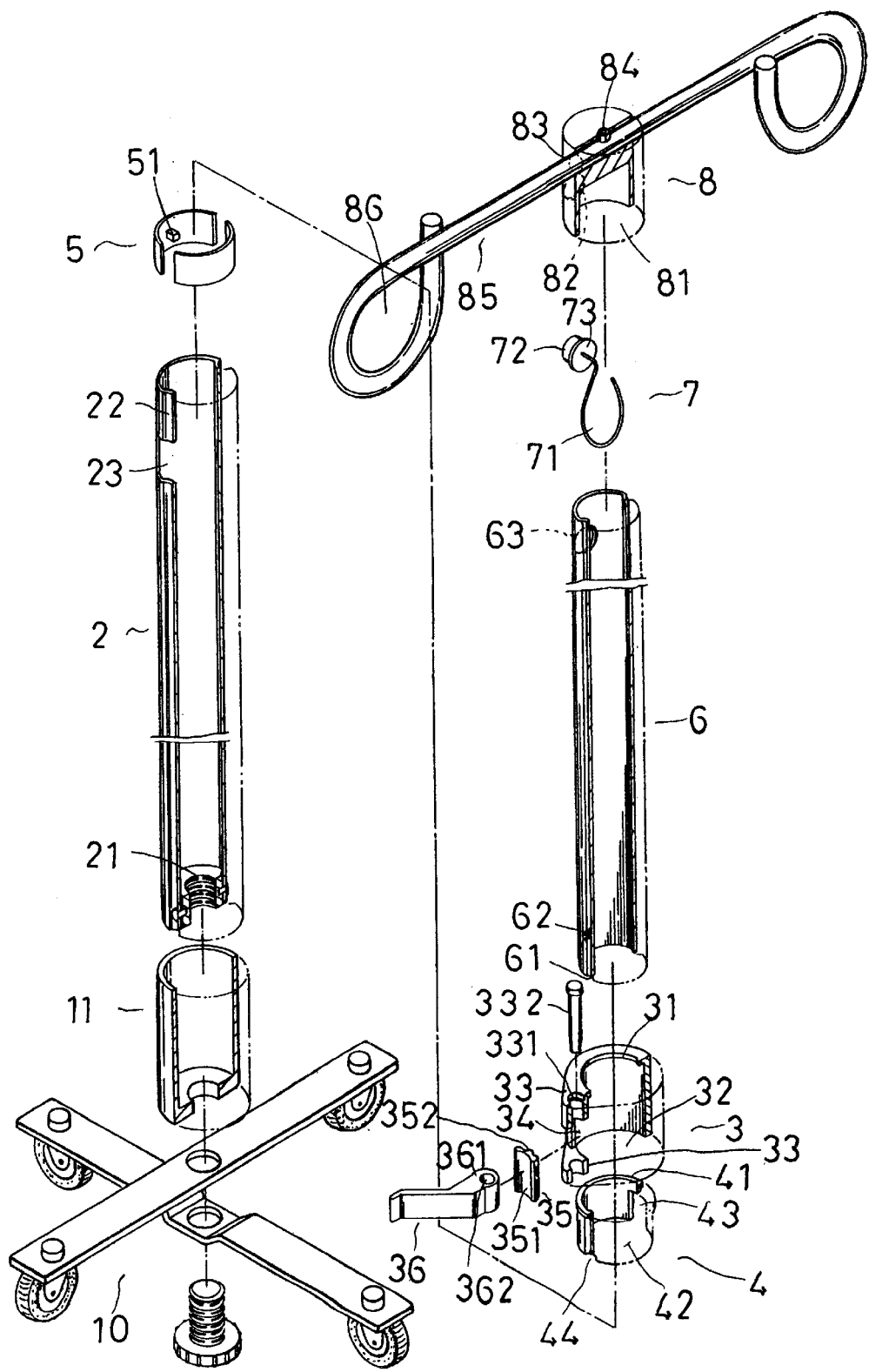
FIG. 1 is an exploded perspective view of a preferred embodiment of a drop-bottle stand in the present invention.

A preferred embodiment of a drop-bottle stand in the present invention, as shown in FIG. 1, includes an outer tube 2, and adjusting sleeve 3, a cylindrical member 4, a two-piece ring 5, an inner movable tube 6, an elastic button 7, an upper connecter 8, a conventional base 10 used in the known conventional one, and a lower connecter 11 used in the known conventional one as main components assembled together.

The outer tube 2 has female threads 21 in a lower end, two longitudinal opposite straight grooves 22 extending in its whole length and a rectangular hole 23 near an upper end.

The adjusting sleeve 3 has an inward-protruding edge 31 formed at a top end, a center hole 32, and a pair of ears 33, one of the ears on an upper end and the other ear on an opposing lower end end—ears 33 on an outer surface and recessed opening 34 is formed between the two opposing ears 33, 33. The two opposing ears 33, 33 have a hole 331 in line for a pin 332 to insert therein. A plate 35 is provided to have a vertical straight ridge 352 in an inner convex side and a concave outer surface 351, able to rest on the reessed opening 34. Then an eccentric arm 36 is provided to have an eccentric portion 361 with a vertical hole 362 and an outer semicirular outer end surface to contact the concave outer surface 361, with the pin 332 protruding the hole 362 and the holes 331, 331 so as to assemble the eccentric arm 36 with the plate 35 and the adjusting sleeve 3 at the same time. Then the eccentric arm can swing for 90 degrees or so.

The cylindrical member 4 has an inner-protruding edge 41 at an upper end, a center hole 42 and a slot 43 in a lower end, and a vertical recess 44.

The two-piece ring 5 is shaped as a ring, cut into two semicircular pieces, and having a projection 51 in an inner surface of each piece.

The inner movable tube 6 has two longitudinal opposite straight grooves 61, 61 extending in its whole length in an outer surface to engage with the two longitudinal opposite grooves 22, 22, and a position hole 62. The inner movable tube 6 has an upper end combined with an upper connecter 8 supporting a top hanging bar with two hooks formed at two ends for hanging a drop bottle.

The elastic button 7 has a U-shaped member 71 with proper elasticity and button body 72 firmly connected with one end of the U-shaped member 71, which is to be placed in an upper end of the inner movable tube 6 with proper tightness, with the button body 72 protruding sidewise out of the hole 63 of the inner movable tube 6 for a certain distance stopped by a flange 73 formed at an inner end of the button body 72.

The upper connecter 8 is shaped cylindrical with a closed upper end and an open lower end, having a center hole 81 opening to the lower end to fit around the upper end of the inner movable tube 6 with proper tightness, a round hole 82 in a peripheral wall to correspond to the hole 63 for the button body 72 of the elastic button 7 to protrude through outward. The upper connecter 8 further has a transverse groove 83 for a top hanging bar 85 to lie therein and fixed firmly with a screw 84.

Figure 2:
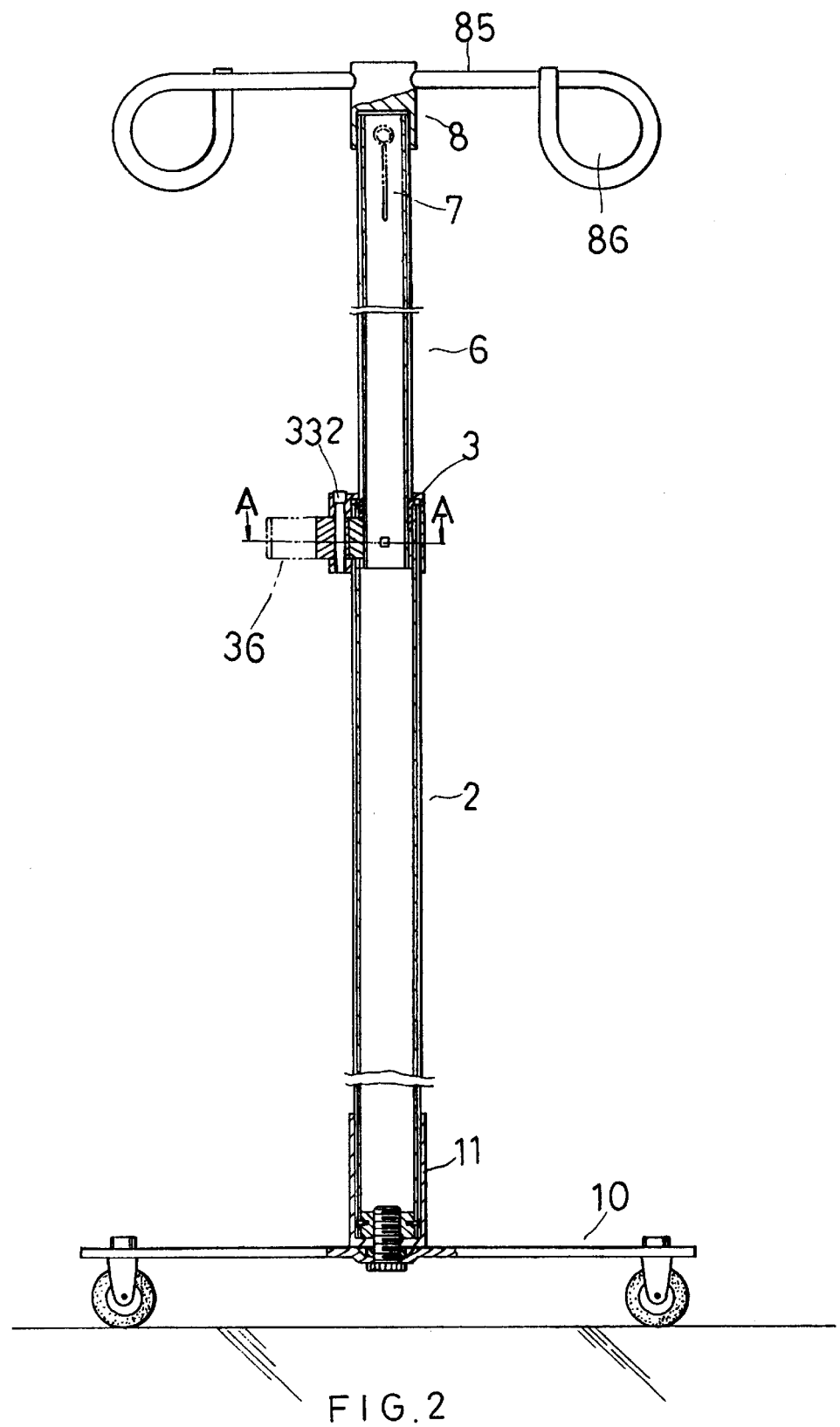
FIG. 2 is a cross-sectional view of the preferred embodiment of a drop-bottle stand in the present invention.

In assembling, firstly, the inner movable tube 6 is made to pass through the adjusting sleeve 3 and the cylindrical member 4, and then the two-piece ring 5 is placed in the position hole 62. After that, the inner tube 6 is inserted in the outer tube 2, and the lower end of the outer tube 2 is placed in the lower connecter 11, assembled with the base 10, as shown in FIG. 2. Meanwhile, the adjusting sleeve 3 and the cylindrical member 4 are firmly fixed with the upper end of the outer tube 2. Then the inner movable tube 6 may be moved slidingly up and down in the outer tube 2, with the cylindrical member 4 guiding the inner tube 6. And the two-piece ring 5 moves up and down in the outer tube 2 as the inner tube 6 moves up and down, with the inner tube 6 moving up and down straight guided by the straight grooves 61, 61 engaging the grooves 22, 22 of the outer tube 2, not rotating therein.

Figure 3:
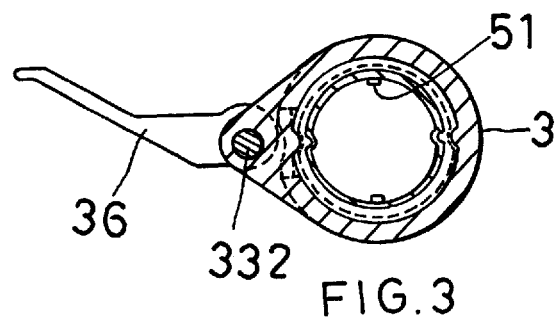
FIG. 3 is an upper view of a adjusting sleeve combined with an eccentric arm in the preferred embodiment of a drop-bottle stand in the present invention, showing the inner movable tube not yet tightened.
Figure 4:
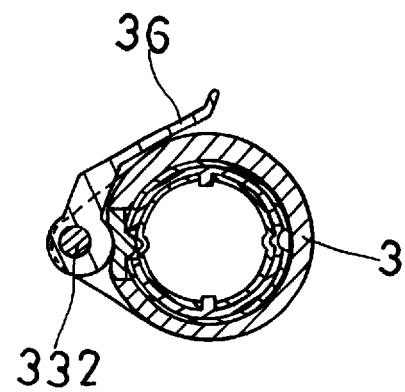
FIG. 4 is an upper view of the adjusting sleeve combined with the eccentric arm in the preferred embodiment of a drop-bottle stand in the present invention, showing the inner movable tube already tightened.
Figure 7:
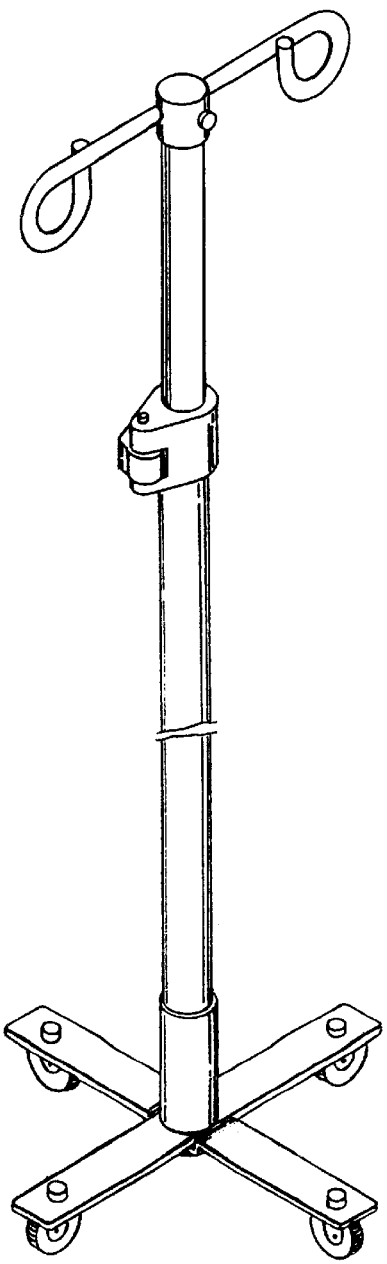
FIG. 7 is a perspective view of the preferred embodiment of a drop-bottle stand in the present invention, showing the inner movable tube already tightened in the highest position.
Figure 8:
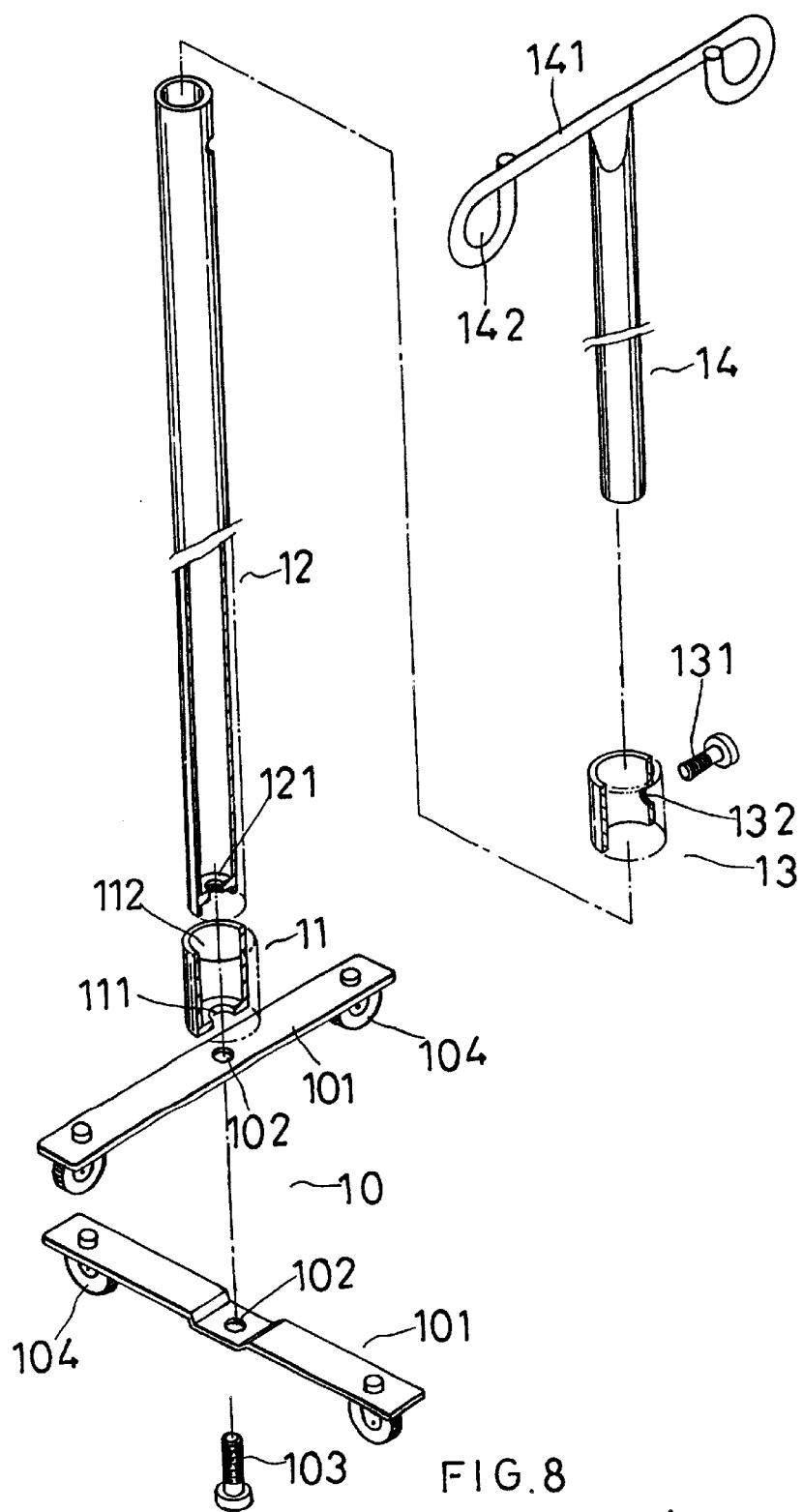
FIG. 8 is an exploded perspective view of a first known conventioanl drop-botttle stand.
Figure 10:
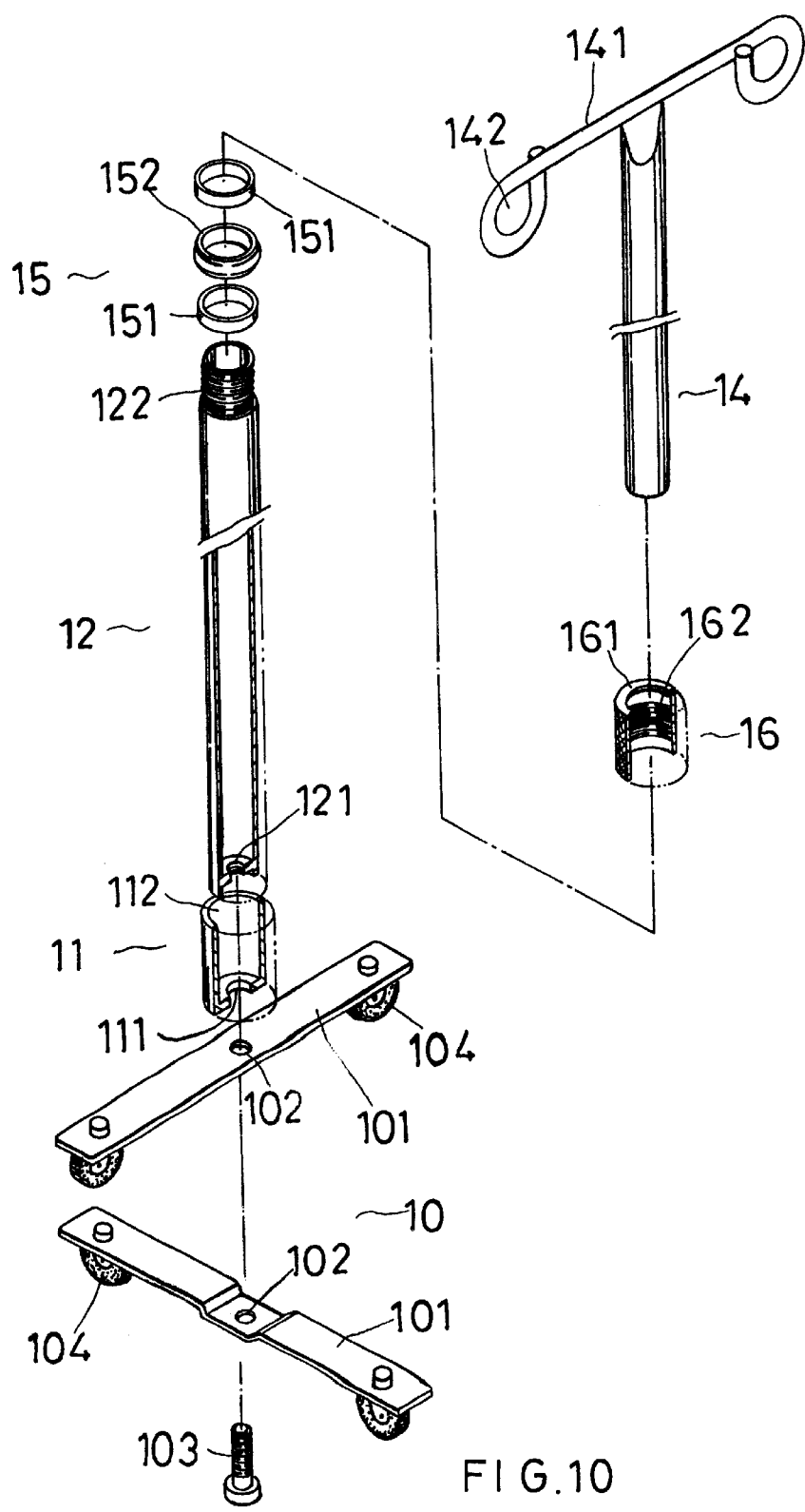
FIG. 10 is an exploded perspective view of a second known conventional drop-bottle stand; and, FIG. 11 a front side view of the second known conventional drop-bottle stand.
Figure 11:
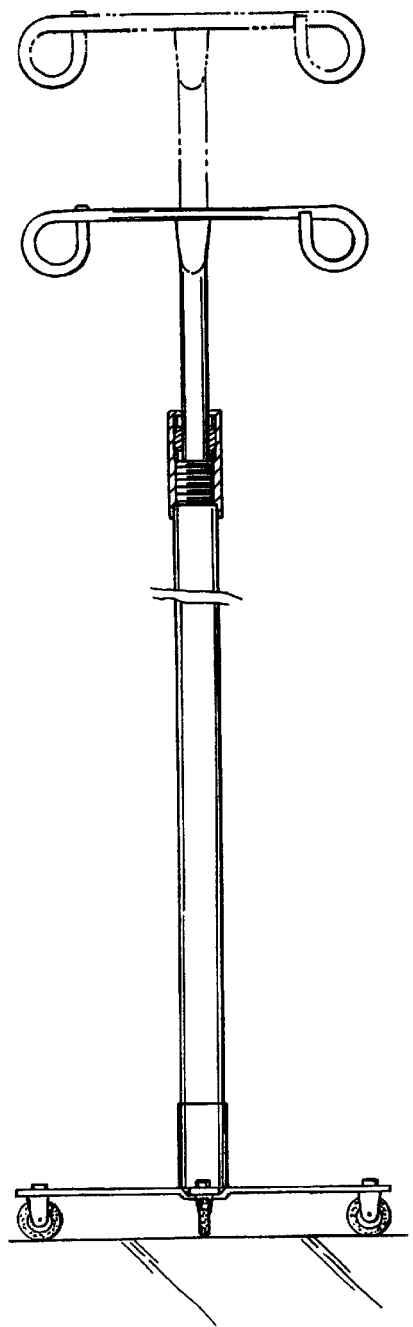
Figure 9:
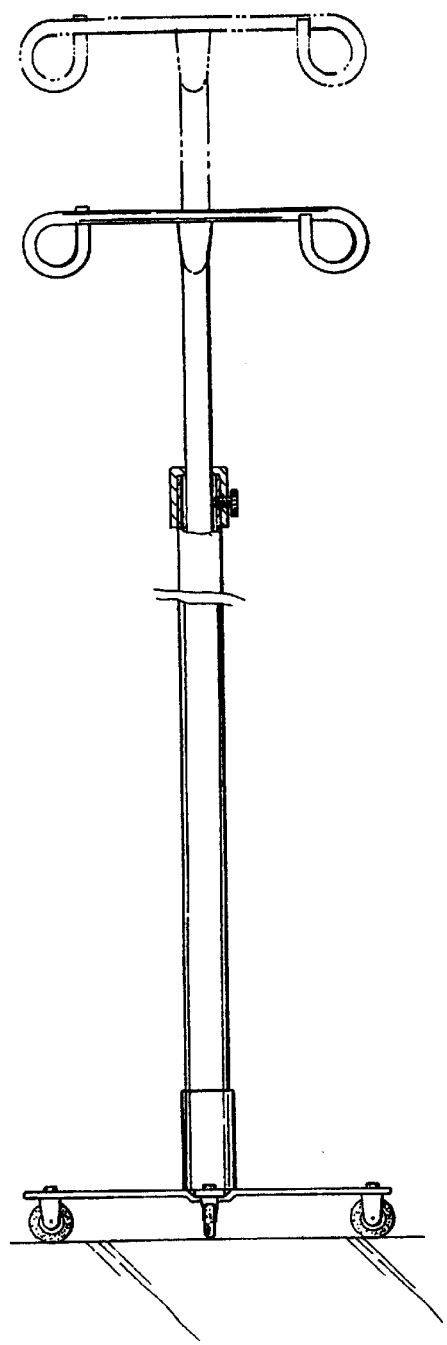
FIG. 9 is a front side view of the first known conventional drop-bottle stand.

Referring to FIGS. 3 and 4, if the eccentric arm 36 is swung to a loosening position shown in FIG. 3, wherein the eccentric portion 361 is separated from the plate 35, not contacting the concave surface 351, the plate 35 and its ridge 352 no longer compresses the inner movable tube 6 so that the tube 6 may be moved to slide up and down for adjusting its position relative to the outer tube 2. After the inner tube 6 is moved to a needed position, the eccentric arm 36 is swung inward to a tightening position, the eccentric arm 36 is swung inward to a tightening position, wherein the eccentric portion 361 contacts forcefully the concave surface 351 of the plate 35, which then compresses the inner tube 6 tightly and kept unmovable at that position as shown in FIGS. 4 and 7.

Figure 5:
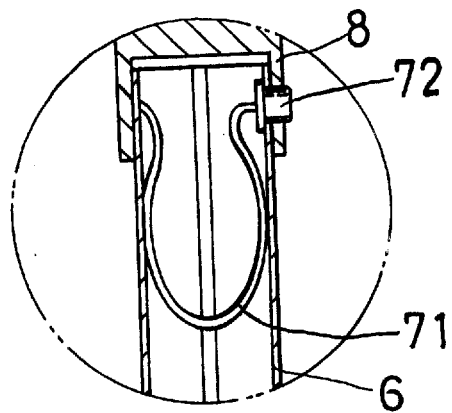
FIG. 5 is a cross-sectional view of an upper connecter combined with an elastic button and the inner movable tube in the preferred embodiment of a drop-bottle stand in the present invention.
Figure 6:
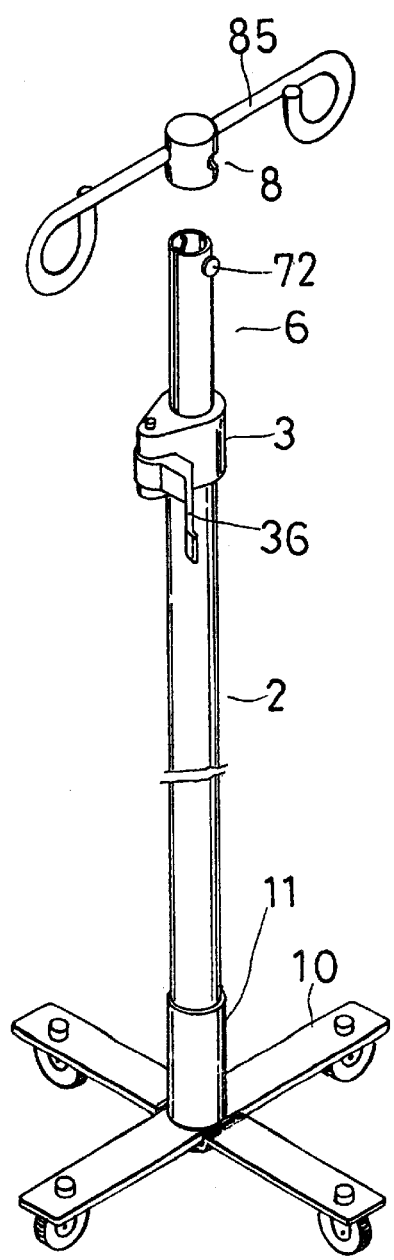
FIG. 6 is a perspective view of the preferred embodiment of a drop-bottle stand in the present invention, showing the inner movable tube not yet tightened and in the lowest position.

As shown in FIGS. 5 and 6, the elastic member 7 is wholly inserted with proper tightness in the upper end of the inner tube 6, with the button body 72 extending sidewise through the hole 63, and the upper connecter 8 is fitted around the upper end of the inner tube 6, with the button body 72 passing through the round hole 82 so as to assemble the upper connecter 8 with the inner tube 6. Then the button body 72 keeps the upper conneter 8 in place, and the top hanging bar 85 may be kept in place, too, as the bar 83 is firmly combined with the upper connecter 8.

As can be understood in the above description, this invention, compared with the known conventional drop-bottle stands, has advantages as follows.

1. Adjusting the position of the inner movable tube can be performed by swinging the eccentric arm for a nearly right angle, from a loosening position to a tightening position or vice versa.

2. The inner movable tube never rotates in moving up and down in the outer tube because of the easy operational features plus the combination of the longitudinal grooves of both the outer tube and the inner tube, even if a drop bottle is being hung up on the hanging bar.

3. The inner movable tube 6 can always be kept clean and smooth by means of the plate 35 compressed by the eccentric arm 36 so as to firmly secure the position of the inner tube 6 adjusted, without using a screw for securing the inner tube as used in the conventional drop-bottle stand. The screw can give rise to recesses and hairy bits.

4. Easily separable structure of the top hanging bar 85 from the inner movable tube 6 enables package dimensions reduce to a minimun, lessening cost for package and transportation.

5. The simple structure of the elastic button 7 can simplify assemblage of the top hanging bar 85 with the inner movable tube 6, even a user may easily assemble them, reducing assembling cost for a manufacturer.

While the preferred embodiments of the invention have been described above, it will be recognized and understood that various modifications may be made therein and the appended claims are intended to cover all such modifications which may fall within the spirit and scope of the invention.

What is claimed is:

1. A drop-bottle stand comprising:

a base consisting of two horizontal elongate plates crossing with each other at respective center portions thereof, each of said elongate plates having a centrally disposed aperture, said elongate plates being connected with a screw passing through said apertures, each said elongate plate having a wheel combined with each of two ends to roll freely on the ground;

a lower connecter having a cylindrical shape and having an open upper side and a lower side with a small center hole formed therein for said screw to pass therethrough from below said base;

an outer tube having female threads formed in a bottom end thereof, said bottom end being disposed in said lower connecter for engaging said screw to secure said outer tube and said lower connecter to said base, said outer tube having two longitudinal grooves formed in an outer surface of opposing sides thereof and a rectangular hole formed therethrough, said two longitudinal grooves forming two longitudinal projections on an inner surface of said outer tube;

an adjusting sleeve having (a) an inner protruding edge formed in an upper end thereof, (b) a centrally disposed hole extending longitudinally therethrough, (c) a pair of longitudinally spaced ears respectively formed adjacent said upper end and a lower end thereof, said pair of ears being positioned in line and each having a vertical hole formed therethrough, (d) a recessed opening located between said pair of ears, (e) a plate having an outer concave surface and a central vertical ridge formed on an inner convex surface and positioned within said recessed opening, (f) an eccentric arm disposed between said pair of ears and having an eccentric portion with a vertical hole formed therein, said vertical hole of said eccentric portion being in aligned relationship with said vertical holes of said pair of ears, and (g) a pin inserted through said vertical holes of said pair of ears and said vertical hole of said eccentric portion of said eccentric arm, said eccentric arm being rotatable through 90 degrees for selective engagement or disengagement of said eccentric portion with respect to said concave surface of said plate, and said adjusting sleeve being fixedly attached to an upper end of said outer tube;

an inner movable tube telescopically disposed within said outer tube and having two longitudinal grooves formed on opposing sides thereof engaged with said two longitudinal projections of said outer tube, said inner movable tube having a positioning hole formed through a side wall thereof;

a cylindrical member having a hole formed centrally therethrough and an inwardly protruding edge formed in an upper end thereof, said cylindrical member having a slot formed in an lower side thereof, a vertically directed recess, fixedly attached to said upper end of said outer tube, and for guiding the inner movable tube within the outer tube;

a two-piece ring having two semicircular pieces respectively provided with a projection extending from an inner surface thereof, disposed within the outer tube and for interlocking with the inner movable tube;

a cylindrically shaped upper connecter having a closed upper end and an open lower end, said upper connector having an aperture formed through a side wall thereof, said closed upper end having a transversely directed groove formed therein and a top hanging bar positioned in said transverse groove and secured therein, said hanging bar having a hook formed on each end thereon, said open end of said upper connecter is fitted around an upper end of said inner movable tube; and, an elastic button formed by a button body and an elastic U-shaped member having one end connected to said button body, said U-shaped member being completely inserted in said upper end of said inner movable tube, said button body extending out through said positioning hole of said inner movable tube for a predetermined distance established by a flange formed in an inner side of said button body and passing through said aperture of said upper connector to prevent said inner movable tube from rotating, and said flange being of larger diameter than said positioning hole of said inner movable tube.

* * * * *